United States Patent
Riley et al.

(10) Patent No.: US 11,800,983 B2
(45) Date of Patent: Oct. 31, 2023

(54) METHOD FOR DETECTING HEMATOMA, PORTABLE DETECTION AND DISCRIMINATION DEVICE AND RELATED SYSTEMS AND APPARATUSES

(71) Applicants: The United States of America, as represented by the Secretary, Department of Health & Human Services, Rockville, MD (US); 02;The Henry M. Jackson Foundation for the Advancement of Military Medicine, Inc., Rockville, MD (US)

(72) Inventors: Jason D. Riley, Kingston (CA); Franck Amyot, Washington, DC (US); Amir H. Gandjbakhche, Potomac, MD (US); James G. Smirniotopoulos, Silver Spring, MD (US); Eric Wassermann, Rockville, MD (US)

(73) Assignees: The United States of America, as represented by the Secretary, Department of Health & Human Services, Bethesda, MD (US); The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 1028 days.

(21) Appl. No.: 15/691,661

(22) Filed: Aug. 30, 2017

(65) Prior Publication Data
US 2018/0008154 A1 Jan. 11, 2018

Related U.S. Application Data

(63) Continuation of application No. 13/516,480, filed as application No. PCT/US2010/060506 on Dec. 15, 2010, now Pat. No. 9,861,287.

(Continued)

(51) Int. Cl.
*A61B 5/02* (2006.01)
*A61B 5/00* (2006.01)
*G01N 21/359* (2014.01)

(52) U.S. Cl.
CPC ........ *A61B 5/02042* (2013.01); *A61B 5/0042* (2013.01); *A61B 5/0059* (2013.01);
(Continued)

(58) Field of Classification Search
CPC .......... A61B 2562/0242; A61B 5/0042; A61B 5/0059; A61B 5/0075; A61B 5/0082;
(Continued)

(56) References Cited

U.S. PATENT DOCUMENTS 5,538,004 A * 7/1996 Bamber ............ G01S 7/52044
128/916
5,954,053 A 9/1999 Chance et al.
(Continued)

FOREIGN PATENT DOCUMENTS

WO WO 2006/121833 11/2006

OTHER PUBLICATIONS

S.P. Gopinath et al., "Near infrared spectroscopy (NIRS) as an early detector of late intracranial hematomas", Intracranial Pressure and Neuromonitoring in Brain Injury, vol. 71, p. 418 (1998).
(Continued)

*Primary Examiner* — Mark D Remaly
(74) *Attorney, Agent, or Firm* — Leydig, Voit & Mayer

(57) ABSTRACT

Featured are methods, apparatus and devices for detecting a hematoma in tissue of a patient. In one aspect, such a method includes emitting near infrared light continuously into the tissue from a non-stationary near infrared light emitter and continuously monitoring the tissue using a non-stationary probe so as to continuously detect reflected light. The near infrared light is emitted at two distances from a brain of the patient, so the emitted light penetrates to two different depths. Such a method also includes applying a ratiometric analysis to the reflected light to distinguish a border between normal tissue and tissue exhibiting blood accumulation.

16 Claims, 4 Drawing Sheets

Related U.S. Application Data

(60) Provisional application No. 61/286,626, filed on Dec. 15, 2009.

(52) U.S. Cl.
CPC .......... *A61B 5/0075* (2013.01); *A61B 5/0082* (2013.01); *A61B 5/4064* (2013.01); *A61B 5/4887* (2013.01); *A61B 5/7282* (2013.01); *A61B 2562/0242* (2013.01); *G01N 21/359* (2013.01)

(58) Field of Classification Search
CPC . A61B 5/02042; A61B 5/4064; A61B 5/4887; A61B 5/7282; G01N 21/359
See application file for complete search history.

(56) References Cited

U.S. PATENT DOCUMENTS

| | | | |
|---|---|---|---|
| 6,134,003 A * | 10/2000 | Tearney | A61B 1/00096 356/479 |
| 7,139,603 B2 | 11/2006 | Chance | |
| 7,610,082 B2 | 10/2009 | Chance | |
| 2005/0043637 A1 | 2/2005 | Caplan | |
| 2007/0073156 A1 | 3/2007 | Zilberman | |
| 2010/0027744 A1 | 2/2010 | Brown et al. | |

OTHER PUBLICATIONS

C.S. Robertson et al., "A new application for near-infrared spectroscopy: Detection of delayed intracranial hematomas after head injury", Journal of Neutrotrauma, 12(4), pp. 591-600 (1995).

Q. Zhang et al., "Study of near infrared technology for intracranial hematoma detection", Journal of Biomedical Optics, 5(2), pp. 206-213 (2000).

S. Goldberg et al., "Near-infrared spectroscopy as a diagnostic tool in patients with suspected stroke or traumatic brain injury", Proceedings of SPIE, vol. 4432, pp. 310-311 (2001).

International Search Report for International Application No. PCT/US2010/060506, dated Mar. 18, 2011.

Written Opinion for International Application No. PCT/US2010/060506, dated Jun. 15, 2012 2005.

International Preliminary Report on Patentability for International Application No. PCT/US2010/060506, dated Jun. 19, 2012.

U.S. Appl. No. 13/516,480, filed Feb. 1, 2013, US 2013-0150726 A1.

\* cited by examiner

METHOD FOR DETECTING HEMATOMA, PORTABLE DETECTION AND DISCRIMINATION DEVICE AND RELATED SYSTEMS AND APPARATUSES

CROSS-REFERENCE TO RELATED APPLICATIONS

This application is a continuation of U.S. patent application Ser. No. 13/516,480, filed 1 Feb. 2013, which is a 35 U.S.C. § 371 U.S. national entry of International Application PCT/US2010/060506 (WO2011/084480) having an International filing date of 15 Dec. 2010, which claims the benefit of U.S. Provisional Application Ser. No. 61/286,626, filed 15 Dec. 2009, all of which are incorporated herein in their entireties by reference.

FIELD OF INVENTION

The present disclosure generally relates to methods, devices and apparatuses for detecting a hematoma, such as a subdural hematoma, more particularly to methods, devices and apparatuses for detecting an intracranial hematoma and yet more particularly to methods, devices and apparatuses for detecting and discriminating a hematoma.

BACKGROUND OF THE INVENTION

A hematoma is a localized collection of extravasated blood (e.g., blood from a ruptured blood vessel or the like), usually clotted, in an organ, space, or tissue; bruises and black eyes are familiar forms that are seldom serious. Hematomas can occur almost anywhere on the body including inside the skull, and are almost always present with a fracture; in minor injuries the blood is absorbed unless infection develops.

Hematomas inside the skull are particularly serious, because they can produce local pressure on the brain. The two most common kinds of these are epidural (outside the brain and its fibrous covering, the dura, but under the skull) and subdural (between the brain and its dura). Other types of hematomas occurring inside the skull include intracerebral (in the brain tissue) and subarachnoid (around the surfaces of the brain, between the dura and arachnoid membranes). Such hematomas can result from a number of causes such as head injury or head trauma as well as due to bleeding disorders or an aneurysm.

Subdural hematomas are usually the result of serious head injury. When a subdural hematoma occurs this way, it is typically called an acute subdural hematoma. Acute subdural hematomas are among the deadliest of head injuries as the bleeding fills the brain area very rapidly, thereby compressing brain tissue, which can lead to brain injury. Also, risk for a subdural hematoma can be increased by one of more of the following; taking anticoagulation medication (e.g., blood thinners including aspirin), long term alcohol abuse, recurrent falls, and repeated head injury. Risk also is increased for the very young and the very old.

Subdural hematomas also can occur from a minor head injury, especially when the injured is elderly. Such hematomas can go unnoticed for a long period of time (e.g., many days to weeks) and are often called a chronic subdural hematoma. With any subdural hematoma, tiny veins between the surface of the brain and its dura stretch and tear, allowing blood to collect. In the elderly, such veins are often stretched because of brain atrophy or shrinkage and thus are more easily injured.

Because of the negative consequences associated with hematomas inside the head or skull, it is necessary to be able to identify and locate such hematomas inside the skull, such that appropriate medical and surgical procedures (e.g., evacuation of the hematoma) can be timely undertaken so as to reduce the chances for mortality and/or worsened outcome in survivors. Such timely undertakening is on the order of about 4 hours from occurrence of the injury and the evacuation of the hematoma.

CT scanning is one imaging technique that can be used to identify and locate traumatic intracranial hematomas. However, all medical facilities (e.g., trauma centers) do not necessarily have immediate CT scanning capability on a 24/7 basis and thus it may not be possible in such cases for a CT scan to be performed so that an identified hematoma can be evacuated within the desired time frame. Also, in emergencies involving head trauma in underdeveloped areas of the world, areas in the US which have limited access to trauma centers having 24/7 CT scanning capability or in areas of the US or the world (e.g., a battlefield) having travel time issues from the site of the injury to the treatment facility; timely identification of patients that require surgery for dealing with the hematoma can be more difficult. Thus, in such settings where a CT scan cannot be performed with the desired time frame, the primary method for identification of patients with hematomas is by means of a neurological exam.

A neurological exam, however, is a poor substitute for a CT scan because no single physical sign can reliably indicate the presence of a hematoma. Focal neurological findings are found in only a fraction of patients with surgical hematomas. Coma has been reported to occur without the occurrence of a surgical hematoma in a large percentage of patients with sever head injury. Although patients with an intracranial hematoma will exhibit increased intracranial pressure (ICP), edema of the optic disk (papilledema), associated with ICP, is uncommon after head injury.

There is found in U.S. Pat. No. 5,954,053, systems that utilize differential measurement of radiation that has migrated through migration paths between two source-detector pairs placed on the head in a manner that each path is localized in a portion of one hemisphere of the brain. Various spectrophotometer systems are also shown for in vivo examination of tissue of a human by measuring changes in electromagnetic radiation scattered and absorbed in a migration path in the tissue. Generally, the spectrophotometer systems comprise a light source for introducing the radiation into the tissue, a detector for detecting radiation that has migrated in the tissue, a processor for processing signals of the detected radiation to create processed data, and a system for determining physiological or pathophysiological changes in the tissue of interest such as bleeding or tumor.

There is found in U.S. Pat. No. 7,139,603, methods and systems that examine tissue positioned between input ports and a detection port. At lease one light source of a visible or infrared wavelength is provided that introduces electromagnetic radiation into the subject. The detection port is optically coupled to a detector that is connected to a detector circuit. Radiation intensities are selected for introduction at the input ports to define a null plane in the tissue. The detection port is positioned relative to the null plane. Radiation is introduced into the subject at the first input port and the radiation that migrates through the tissue is detected. The detector circuit stores a first detector signal corresponding to the first detected radiation. Radiation is introduced at the second input port and is detected. The first detector signal is subtracted from a second detector signal corresponding to the second detected radiation to obtain processed data.

There is found in U.S. Pat. No. 7,610,082, an optical examination technique that employs an optical system for in vivo non-invasive transcranial examination of brain tissue of a subject. The optical system includes an optical module arranged for placement on the exterior of the head, a controller and a processor. The optical module includes an array of optical input ports and optical detection ports located in a selected geometrical pattern to provide a multiplicity of photon migration paths inside the biological tissue. Each optical input port is constructed to introduce into the examined tissue visible or infrared light emitted from a light source. Each optical detection port is constructed to provide light from the tissue to a light detector. The controller is constructed and arranged to activate one or several light sources and light detectors so that the light detector detects light that has migrated over at least one of the photon migration paths. The processor receives signals corresponding to the detected light and forms at least two data sets, a first of said data sets representing blood volume in the examined tissue region and a second of said data sets representing blood oxygenation of the examined tissue. The processor is arranged to correlate the first and second data sets to detect abnormal tissue in the examined tissue.

There is found in International Publication No. WO 2006/121833, a system and method for determining a brain hematoma including a handheld device for emitting and detecting radiation with a removable light guide assembly. The method for determining a brain hematoma condition includes determining optical density of various regions of the brain using near infrared spectroscopy.

In the above identified International Publication, the described device is positioned at a specific location of the head and data is acquired using the device. After acquiring data at this location, the device is re-located to another location of the head and another set of data is acquired at the new location. This relocation of the device and acquiring a set of data is repeated until the device has been placed at all possible or desired locations of the head.

It thus continues to be desirable to provide methods, devices, apparatuses for detecting hematomas in tissues of a patient. More particularly it continues to be desirable to provide such methods, devices and apparatuses for detecting and identifying a hematoma, yet more particularly the type of hematoma inside the head of the patient. It also would be desirable to provide such methods, device and apparatuses that allow a clinician. medical personnel, emergency medical technician, medic/coreman or the like to detect such a hematoma without requiring the use of sophisticated imaging systems or techniques such as CAT scan or MRI systems and in a wide range of settings including hospital ER settings and usage in the battlefield, rural areas or in less developed areas of the world. Such devices preferably would be simple in construction and less costly than prior art devices and such methods would not require highly skilled users to utilize the device.

SUMMARY OF THE INVENTION

The present disclosure features methods, apparatus and devices for detecting a hematoma in tissue of a patient. Such methods, apparatus and devices advantageously provide a mechanism for detecting hematomas such as an intracranial arachnoid hemorrhage (SAH) or subdural hematoma (SDH) not otherwise detectable without the use of highly skilled clinicians and/or large scale imaging scanners such as MRI scanners and CAT scanners. Such methods and devices of the present disclosure also are advantageous as they allow the clinician, medical personnel, EMT or medic to perform an initial assessment of patient in a wide range of settings as well as with relatively speaking short enough time periods after occurrence of the accident or injury so as to minimize the risk of death or complications.

Such methods, apparatuses and devices of the present disclosure provides a triage tool to prioritize expensive CT scans. If the use of the device reduces the need for CT scans by 5% for example, the cost savings would hugely beneficial. Also, because of the relatively small size of a detection device according to the present disclosure, the device also would be advantageous in combat critical care or third world care situations where CT scan may not be readily available. In such cases the ability to roughly locate the center of a hematoma using the detection device of the present disclosure provides a means for localizing the hematoma for surgical intervention and thus improving the ability to save a life from a hematoma type injury.

According to an aspect of the present disclosure, there is featured a method for detecting a hematoma. Such a method includes emitting near infrared light and directing the emitted light towards tissue of a patient, measuring reflected light corresponding to two depths of penetration, obtaining a ratiometric measure of the reflected light corresponding to the two depths of penetration; and determining from the obtained ratiometric measure at least the presence of a blood event. Such a blood event is representative of a blood-tissue injury and more particularly includes an intracranial arachnoid hemorrhage a subdural hematoma or an epidural hematoma.

In embodiments, such methods further include moving an emitter of the near infrared light and a reflected light detection section for detecting the reflected light along an external surface of the tissue, and performing said steps of emitting, measuring and determining during said step of moving.

In such methods, the ratiometric measure is representative of a ratio of densities representing the reflected light of the two penetration depths. Also such determining includes evaluating the ratiometric measure to distinguish between normal tissue and tissue exhibiting blood accumulation.

In yet further embodiments, such methods further include providing a detection device including a near infrared light emitting section and a reflected light detection section. The near infrared light emitting section is configured and arranged so that the near infrared light being emitted penetrates to two different depths in the patient and the reflected light detection section is configured and arranged so as to separately detect reflect light being reflected from the two depths. In more particular embodiments, the near infrared light emitting section is configured and arranged so as to emit a first light having a wavelength at or about a first wavelength, the first light penetrating to a first depth and to emit a second light having another wavelength at or about a second wavelength, the second light penetrating to a second depth and the reflected light detection section is configured and arranged to separately detect reflected light corresponding to the first light and reflected light corresponding to the second light.

In yet more particular embodiments, the first wavelength and the second wavelength are on either side of 800 nm. Alternatively, the first light has a wavelength longer than 800 nm and the second light has a wavelength shorter than 800 nm.

In yet more particular embodiments, the emitter/emitting section includes two discrete light sources that each emit near infrared light and the reflected light detection section includes two bands of detection elements that are separated from the discrete light sources at two different distances to detect the reflected light. The two bands of detection elements are arranged so that each band of detection elements are positioned so as to detect reflected light coming from the two different depths inside the head, corresponding to two sensitivity bands inside the head. In further embodiments, one of the emitted lights penetrates the skull and the other of the emitted lights penetrates further inside the skull so as to in effect interrogate the subarachnoid region.

In yet further embodiments, such methods further include moving the emitter and the reflected light detection section along an external surface of the tissue from a start to an end position, where said measuring includes measuring the reflected light in a time sequence during said moving. Such methods also include successively determining in the time sequence, positions of the emitter and reflected light detection section with respect to the tissue during said moving from the first position to the end position.

In yet further embodiments, such methods include creating a volumetric image using the acquired time sequence of measured reflected light corresponding to the two depths and the determined positions in a time sequence.

In yet further embodiments, such a step of obtaining includes obtaining a ratiometric measure of the reflected light corresponding to the two depths of penetration for each time sequenced acquired reflected light. Also such a step of determining includes determining from each obtained ratiometric measure of the time sequenced acquired reflected light one of (a) the presence of the blood event, (b) the absence of the blood event, or (c) the possibility of the presence of a blood event.

In the case where it is determined that there is a possibility of a blood event, the medical personnel can perform additional testing or screening, including using a more sophisticated imaging technique (e.g., MRI, CAT) to determine the presence of a hematoma. In this way, the methods of the present disclosure can be used in appropriate settings to triage injured people so as to allow the medical personnel to determine who does or does not require further screening or imaging to determine location and other features of a hematoma as well as the type of hematoma and thus also providing an indicator of the possible severity of the injury. Such information also can be used to determine the need to risk immediate evacuate a person on a battlefield or accident site as well as the mode of transportation.

According to another aspect of the present disclosure, there is featured another method for detecting a hematoma in tissue of a patient. Such a method includes emitting near infrared light continuously into the tissue from a non-stationary near infrared light emitter and continuously monitoring the tissue using a non-stationary probe so as to continuously detect reflected light. The near infrared light is emitted at two distances from a brain of the patient, so the emitted light penetrates to two different depths. Such a method also includes applying a ratiometric analysis to the reflected light to distinguish a border between normal tissue and tissue exhibiting blood accumulation.

In further embodiments, such methods include applying a ratiometric analysis to the reflected light to distinguish a border between normal tissue and tissue exhibiting blood accumulation. Such a ratiometric measure is representative of a ratio of densities representing the reflected light of the two different depths.

In further embodiments, the non-stationary emitter is configured and arranged so as to emit light having a wavelength at or about a first wavelength, for penetrating to one of the two distances and to emit a light having another wavelength at or about a second wavelength, for penetrating to the other of the two distances. Also, the non-stationary probe is configured and arranged to separately detect reflected light corresponding to the first wavelength and reflected light corresponding to the second wavelength.

In yet more particular embodiments, the emitting section includes two discrete light sources that each emit near infrared light and the detection section includes two bands of detection elements that are separated from the discrete light sources at two different distances to detect the reflected light. The two bands of detection elements are arranged so that each band of detection elements are positioned so as to detect reflected light coming from the two different depths inside the head, corresponding to two sensitivity bands inside the head. In further embodiments, one of the emitted lights penetrates the skull and the other of the emitted lights penetrates further inside the skull so as to in effect interrogate the subarachnoid region.

According to yet another aspect of the present disclosure, there is featured an apparatus for detecting a hematoma in tissue of a patient. Such an apparatus includes a detection device that emits near infrared light into the tissue and which provides outputs correspond to detected reflected light and an analysis section operably coupled to the detection device that determines at least the presence of a blood event from the detection device outputs. In yet more particular embodiments, the analysis section is configured and arranged to apply a ratiometric analysis to the reflected light to distinguish between normal tissue and tissue containing accumulated blood.

Such a detection device includes a near infrared light emitting section and a detection section. The near infrared light emitting section is configured and arranged so the near infrared light is emitted at two distances from a brain of the patient and so the emitted light penetrates to two different depths. The detection section is configured and arranged so as to separately detect reflected light from the two different depths.

In yet further embodiments, the near infrared light emitting section is configured and arranged so as to emit light at or about a first wavelength, for penetrating to one of the two different depths and to emit a light at or about a second wavelength, for penetrating to the other of the two different distances. Also, the detection section is configured and arranged to separately detect reflected light at or about the first wavelength and reflected light at or about the second wavelength.

In yet more particular embodiments, the emitting section includes two discrete light sources that each emit near infrared light and the detection section includes two bands of detection elements that are separated from the discrete light sources at two different distances to detect the reflected light. The two bands of detection elements are arranged so that each band of detection elements are positioned so as to detect reflected light coming from the two different depths inside the head, corresponding to two sensitivity bands inside the head. In further embodiments, one of the emitted lights penetrates the skull and the other of the emitted lights penetrates further inside the skull so as to in effect interrogate the subarachnoid region.

In yet further embodiments, the detection device further includes a plurality of tracking mechanisms that each continuously provide in a time sequence outputs as the detection device is moved along an external surface of the tissue. The analysis section is further configured and arranged so as to determine time sequenced positions of the detection device from the time sequenced outputs from the tracking mechanisms.

In yet further embodiments, such an apparatus further include an imaging section operably coupled to the analysis section. The analysis section provides outputs corresponding to the determined time sequenced positions of the detection device. The imaging section is configured and arranged to provide a volumetric image using the acquired time sequence of measured reflected light corresponding to the two different depths and the determined time sequence positions.

While the methods, apparatuses and devices of the present disclosure are described in connection with detecting and localizing hematomas, the detection device, methods and apparatuses of the present disclosure are adaptable for use to detect any heavy optical contrast agent that is located in a near surface (few diffusion lengths) of an object or a subsurface location of an object.

Other aspects and embodiments of the disclosure are discussed below.

Definitions

The instant disclosure is most clearly understood with reference to the following definitions:

Unilateral hematoma shall be understood to mean a hematoma inside the head and in which blood collection or accumulation takes place on one side of the head.

Bilateral hematoma shall be understood to mean a hematoma inside the head and in which blood collection or accumulation takes place on both sides of the head.

An epidural hematoma shall be understood to mean a hematoma inside the head and where the blood collects or accumulates outside the brain and its fibrous covering, the dura, but under the skull.

A subdural hematoma (SDH) shall be understood to mean a hematoma inside the head and where the blood collects or accumulates between the brain and its dura.

An intracerebral hematoma shall be understood to mean a hematoma inside the head and where the blood collects or accumulates in the brain tissue.

A subarachnoid hematoma or hemorrhage (SAH) shall be understood to mean a hematoma inside the head and where the blood collects or accumulates around the surfaces of the brain, between the dura and arachnoid membranes.

The term patient shall be understood to include mammalians including human beings as well as other members of the animal kingdom.

USP shall be understood to mean U.S. patent Number, namely a U.S. patent granted by the U.S. Patent and Trademark Office.

As used in the specification and claims, the singular form "a", "an" and "the" include plural references unless the context clearly dictates otherwise.

ASIC shall be understood to mean application specific integrated circuit.

BRIEF DESCRIPTION OF THE DRAWING

For a fuller understanding of the nature and desired objects of the present dislosure, reference is made to the following detailed description taken in conjunction with the accompanying drawing figures wherein like reference character denote corresponding parts throughout the several views and wherein.

DETAILED DESCRIPTION OF THE INVENTION

Figure 1A:
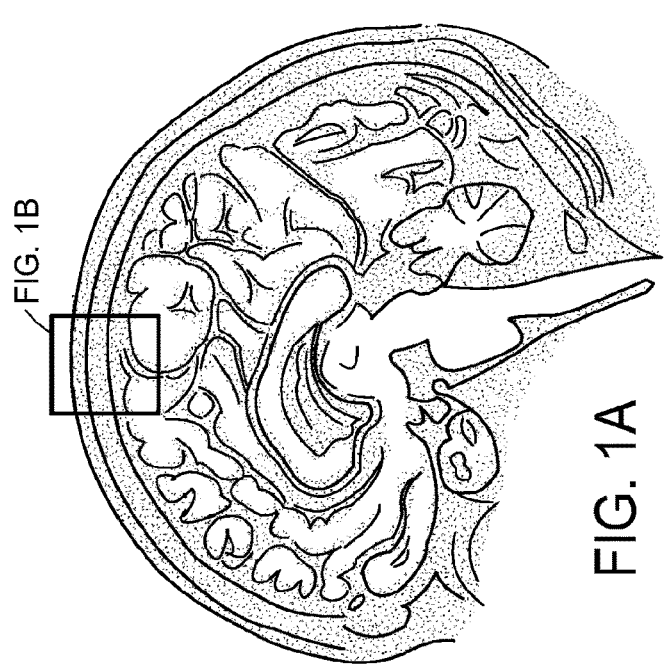
FIGS. 1A and 1B are illustrative views of the general anatomical configuration of the skull of a human.
Figure 1B:
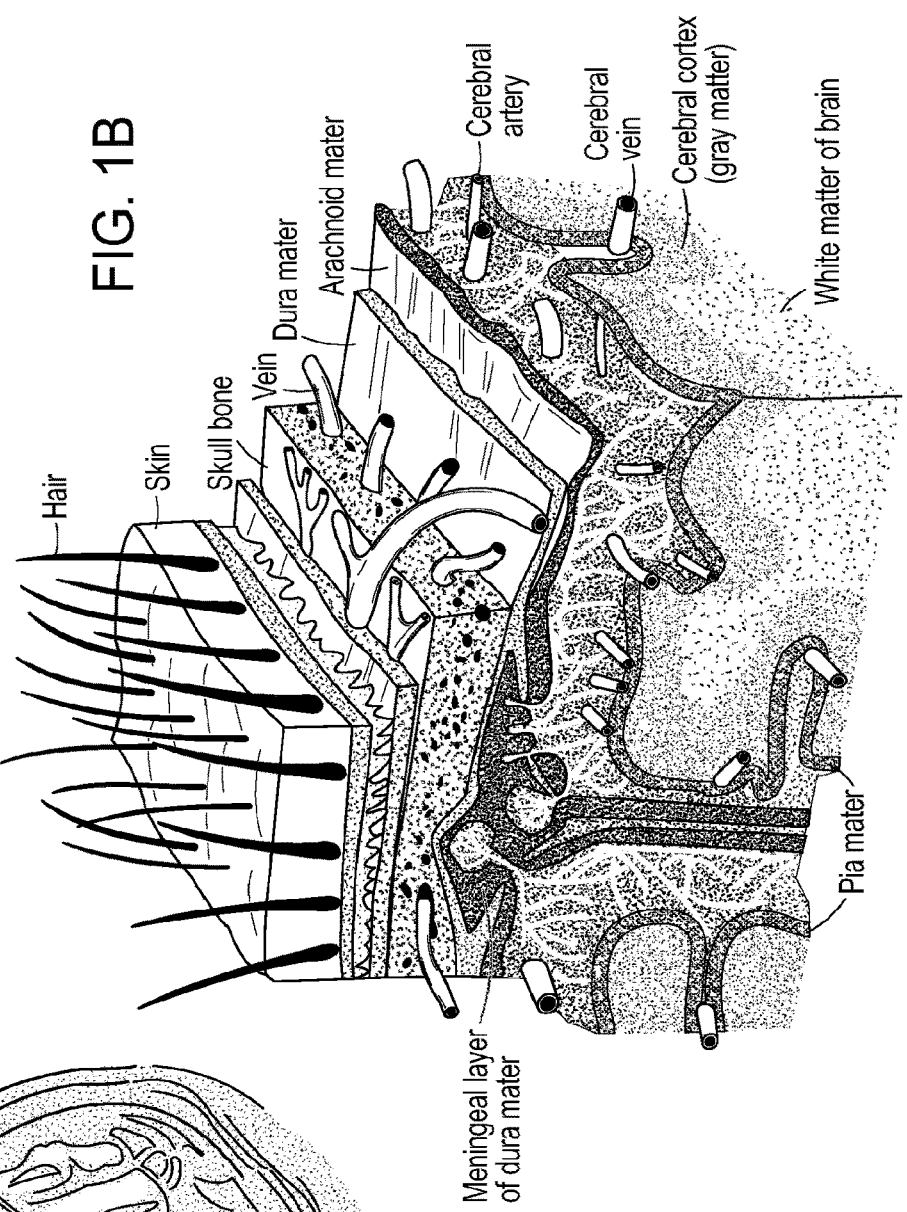

Referring now to the various figures of the drawing wherein like reference characters refer to like parts, there is shown in FIGS. 1A and 1B illustrative views of the general anatomical configuration of the skull of a human. As shown, three membranes are located between the skull and the brain which serve to cushion and protect the brain. These layers are the dura matter (dura), the arachnoid and the pita mater (pita). These three membranes envelope the brain.

The pia is delicate and vascular, the arachnoid is thin and separates the pia from the dura. The dura is a tough fibrous membrane that envelopes the brain and its more delicate structures. When the vessels of the pia are rupture such as a result of trauma or other reason, the escaping or leaking blood accumulates in a localized fashion within the series of membranes to form either a SAH or SDH. Because the skull shields the area where the blood is accumulating, an EMT, clinician or emergency room personnel cannot detect the presence of the hematoma (SAH or SDH) by routine visual inspection. Thus, as indicated herein an SDH for example could go undetected during such a routine visual inspection and could lead to severe consequences.

In its broadest aspects the present disclosure features methods for detecting hematomas more particularly hematomas inside the skull including SAH and SDH as well as being able to identify the particular type of hematoma. The present disclosure also features devices, apparatuses and systems for detection and/or visualizing such hematomas. As described herein, in more particular embodiments the detection device is preferably hand held so as to allow the use of the device in a clinical setting and a non-clinical setting (e.g., rural, battlefield, accident site) by people having a wide range of qualifications (e.g., emergency room personnel, EMTs, medics).

Such methods, devices, apparatuses and systems of the present disclosure utilize the properties of diffuse tissue optics to detect and determine the presence of hematomas. In diffuse tissue optics, it is known that blood accumulating in tissue causes a contrast shift in back reflected light from the tissue. In prior art techniques, people have been trying to use such measures for complex issues such as neuro-imaging of subtle changes for cancer detection. In the present disclosure, however, one is looking for a very gross change in tissue blood volume which is what one would expect in the case of a hematoma.

Such a detection device also advantageous allows the user (doctor, EMT, medic, or medical personnel) to determine at a scene of an accident, in an emergency room or other locations, where there is limited to no ready access to a CT scanner, to diagnose whether a patient with a traumatic brain injury has sustained a hematoma and also allow the user to determine if the hematoma is subdural or epidural. Moreover, such methods, devices an apparatuses of the present disclosure are such as to allow the user to transfer data and/or information to a computer such as for example a laptop, to create a 3d surface image of the scanned volumes and or so as to allow the user to have the location of the hematoma to be displayed.

Such methods, apparatuses and systems of the present disclosure also embody a detection device that collects data for detecting a hematoma, as it is being moved along the outer surface of head. In conventional techniques or methods, data is collected using a stationary probe that has to repositioned at different locations for data acquisition.

Such methods, devices, apparatus and/or systems also provide a mechanism by which medical personnel, EMTs, medics and the like can screen or triage patients or victims having head injuries. Such screening or triage should allow the personnel to determine those patients who should undergo more sophisticated imaging procedures (e.g., CAT scan), as well making an assessment as to the as the severity of the possible injury to determine, if necessary the order in which patients will be imaged.

Figure 2:
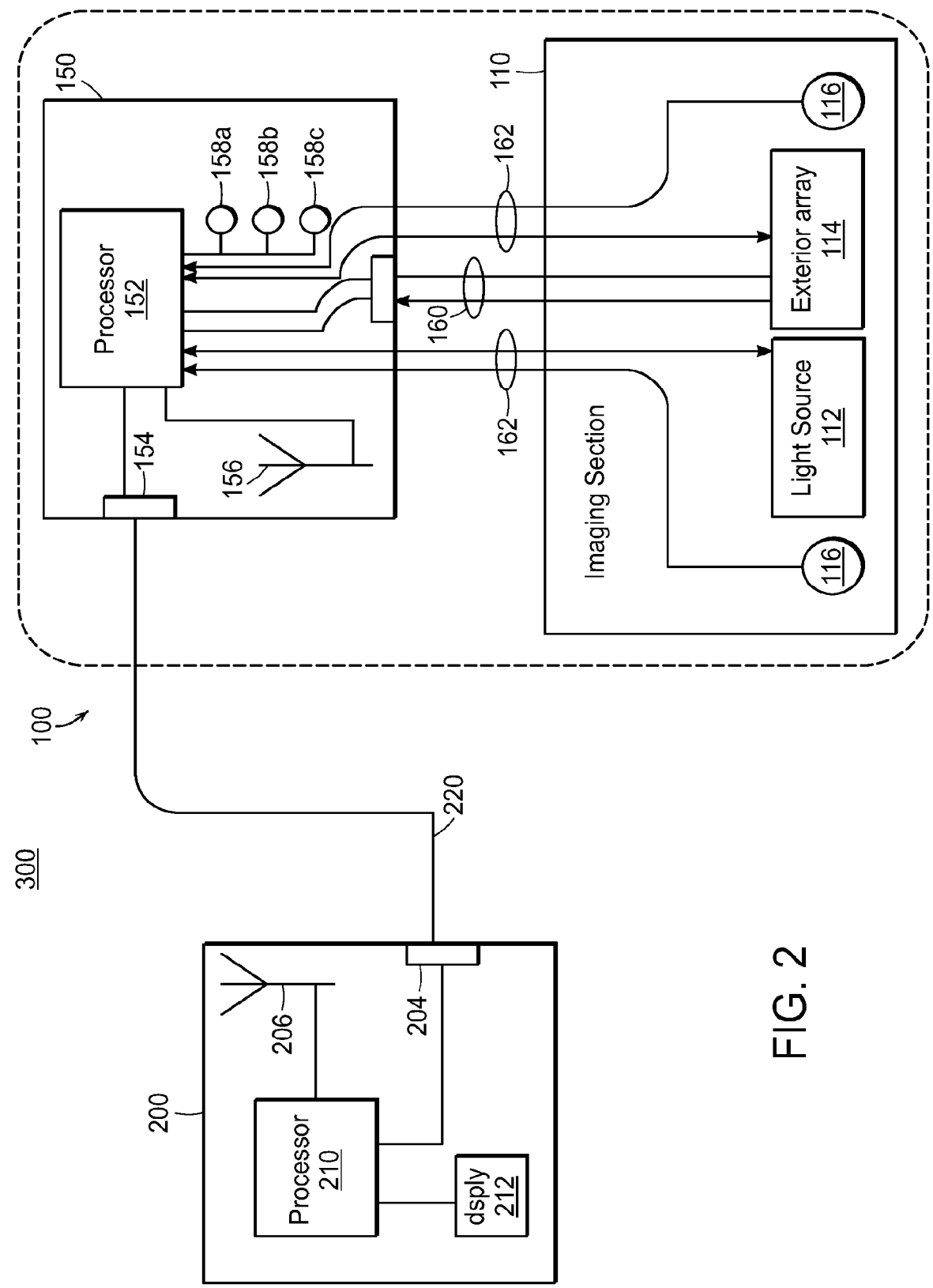
FIG. 2 is a schematic block diagram view of an apparatus according to the present disclosure for detecting a hematoma and including a handheld detector according to the present disclosure.
Figure 3:
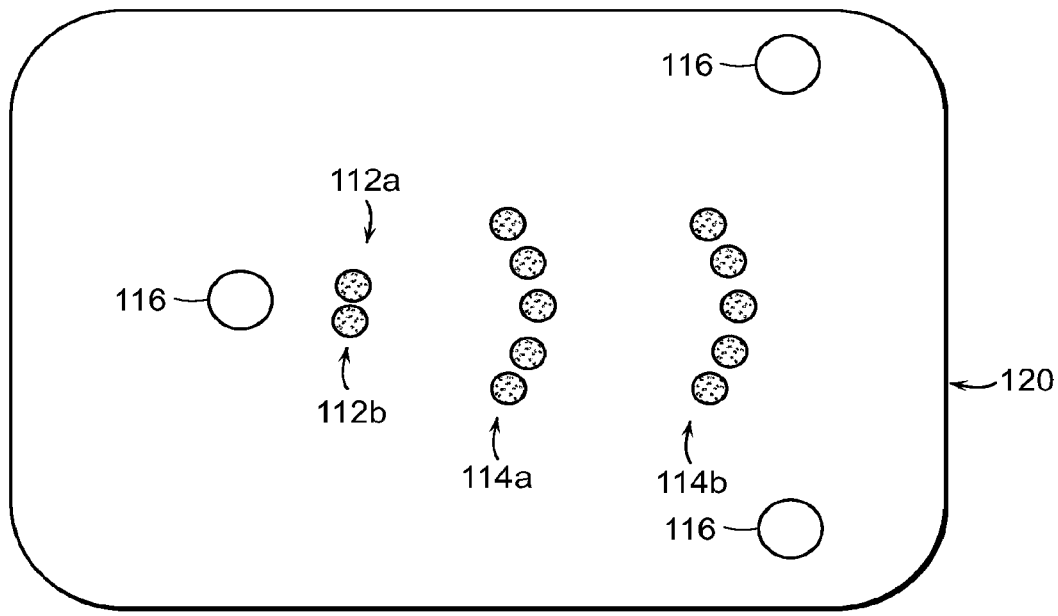
FIG. 3 is an illustrative bottom view of the imaging head portion or imaging section of a handheld detector according to the present disclosure.

Referring now to FIG. 2, there is shown a schematic block diagram view of an apparatus 300 or system according to the present disclosure for detecting hematoma, which apparatus 300 includes a detector 100 and a medical station 200 or data processing station according to the present disclosure. The medical station 200 is operably and communicatively coupled to the detector 100 using any of a number of techniques known to those skilled in the art so that the data that was acquired by the detector 100 is communicated to the medical station. As described further herein, in further embodiments such transferred data is processed and/or manipulated to generate or create a volumetric image of the volume which had been scanned for observation by medical personnel. The medical station 200 also is configurable so the transferred data and/or the created volumetric image is uploaded into the medical records for the patient or otherwise saved for record keeping purposes. Reference also is made to FIG. 3 which provides an illustrative exemplary bottom view of the imaging head portion or imaging section 110 of a detector 100 according to the present disclosure.

Figure 4:
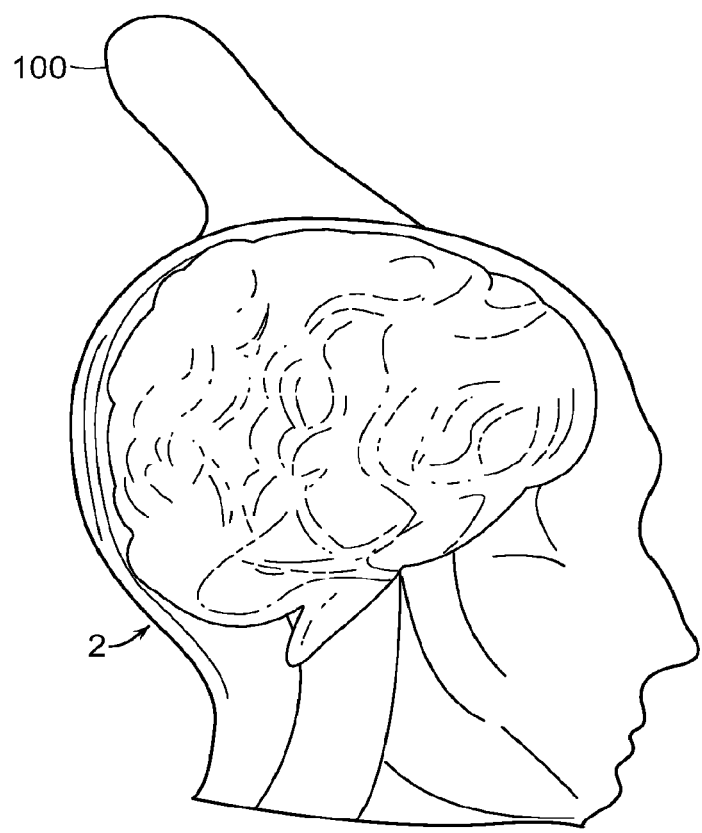
FIG. 4 is an illustrative view showing a handheld detector according to the present disclosure when disposed on a head of a patient.

The detector 100 includes an imaging section 110 and a control and monitoring section 150 that is operably and communicatively coupled to the imaging section. In one embodiment, the imaging section and the control and monitoring section are arranged so as to form a unitary structure that is preferably arranged so that the detector 100 is handheld, such as shown in FIG. 4. In such an application, and as illustrated in FIG. 4, the bottom surface of the detector 100 is laid onto the head of the patient such that the user can move the detector laterally across the scalp of the head while continuously collecting image data as described further herein. In such an application, the detector 100 includes a power supply (not shown) such as a battery or a capacitor in which is stored energy sufficient to perform the imaging process.

In another embodiment, the detector 100 is formed in two separate parts, the imaging section 110 and the control and monitoring section 150. In this embodiment, the imaging section 110 is configured so as to be handheld and also so as to be moved along the scalp of the patient much as described above. In this embodiment, the control and monitoring section 150 is operably coupled to the imaging section 110 using one or more optical or electrical cables 160, 162 so that the control and monitoring section is remote from the imaging section.

In one illustrative embodiment, the control and monitoring section 150 is disposed in a housing or structure that is secured about the waist of the user. As with the other above-described embodiment, the power supply (not shown) is embodied within the control and monitoring section 150 or is housed in a separate structure. Alternatively, the control and monitoring section 150 is remote from the imaging section 100 and is disposed, for example, on a table or platform. The control and monitoring section 150 also is operably coupled to the imaging section by cables 160, 162. In this alternative embodiment, the power supply is portable as described above or the control and monitoring section 150 is arranged so as to receive power from a stationary power supply.

The control and monitoring section 150 includes the electronics and functionalities that control the operation of the imaging section 110, to control acquisition of image data from the imaging section, to perform the calculation procedures and/or techniques for determining the presence of a hematoma as well as the type of hematoma and providing visual queues to the user to indicate the presence or lack thereof of a hematoma. In more particular embodiments, the control and monitoring section 150 includes processing circuitry 152 as is known to those skilled in the art that is configurable to perform the above described functions as well as control data or information transfer between the medical station 200 and the detector 100.

As is known to those skilled in the art such processing circuitry 152 includes a processor or other circuit element (e.g., ASIC), RAM, and one or more software programs that is/are executed in the processor so as to perform the control and processing functions of the medical station. The control and monitoring section also can be configured so as to be operably coupled to any of a number of ancillary devices or functionalities, such as for example, a keyboard, mouse, pointer, voice recognition input device and the like that provide a mechanism to allow the user to update the software or setup the detector 100 so it can perform the imaging process for a given patient while taking into account any patient parameters or environmental conditions so as to optimize the data acquisition process. Such a control and monitoring device also is configurable so as to be operably coupled to a display device, such as described below foe use in connection with the use of an ancillary device.

The control and monitoring section 150 also includes one or more communication mechanisms 154, 156 that are operable coupled to the processing circuitry 152 so that the processing circuitry can receive and/or transmit data or information. In illustrative embodiments, the control and monitoring section 150 includes an I/O port(s) 154 as is known to those skilled in the art, whereby the detector 100 can be operably and communicatively coupled to the medical station 200. In exemplary embodiments, the I/O port 204 is a USB or firewire type of I/O port so that the detector 100 can be connected to the medical station 200 via a hard line 220.

In further illustrative embodiments, the control and monitoring section 150 includes a wireless transmission device 156, such as for example and transceiver and an antenna, that communicates with the detector without the need for a hardline. Such a transmission device 156 is operably coupled to a complimentary transmission device 206 provided with the medical station 200. In further embodiments, such transmission devices 206, 156 utilize RF or IR signal techniques for communication. In more particular embodiments, the transmission devices embody well known bluetooth transmission techniques for such wireless communications. It also should be recognized that while the detector 100 is composed of two parts, a control and monitoring section 150 and an imaging section 110, it is within the skill of those knowledgeable in the arts to configure each so as to embody wireless communication techniques to transmit and/or receive communication commands, data and/or information between the two sections.

In further embodiments, the imaging section 110 is configured so as to include a plurality, more particularly three or more tracking devices 116 (see FIG. 3) that are arranged and configured so as to provide data or information back to the control and monitoring section 150, more specifically the processing circuitry 152 thereof. In illustrative embodiments, the tracking devices are rollerballs as are known to those skilled in the art. The motion of the rollerballs is tracked as the detector 100, more specifically the imaging section 110 thereof, moves along the scalp of the head 2. In more particular embodiments, such a trackball system embodies a Kahlman filter so as to allow for the motion of the three points corresponding to gradually refine and improve the estimate of the geometry. In more particular embodiments, the processing circuitry 152 of the control and monitoring section 150 includes a software program embodying any one of a number of algorithms known to those skilled in the art, which can develop the tracking information corresponding to the movement of the rollerballs 116 and thus the movement of the imaging section 110.

Figure 5:
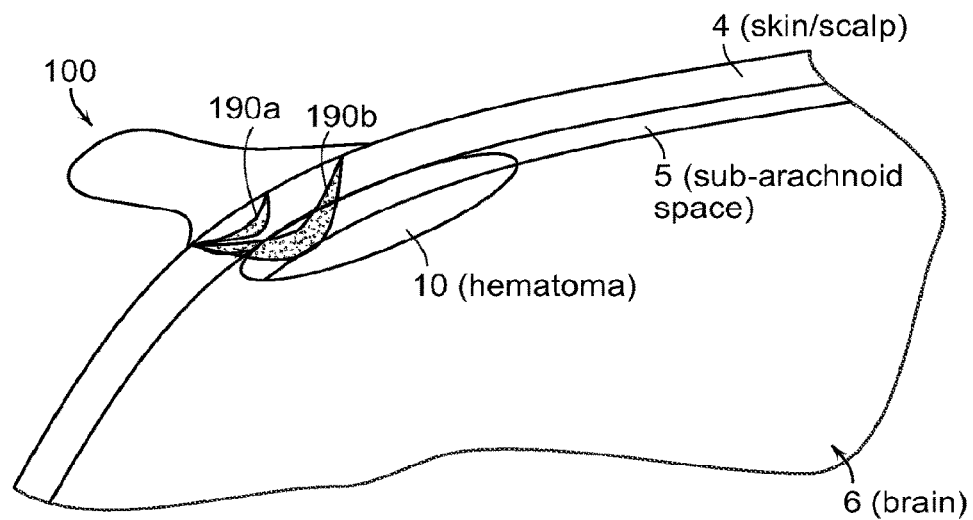
FIG. 5 is an illustrative view of a portion of a head and a handheld detector according to the present disclosure to illustrate the ratiometric aspect embodied in the detector and methods of the present disclosure.

As indicated herein, the tracking data from movement of the rollerballs along the surface of the scalp 4 (FIG. 5) in conjunction with the data being acquired as the imaging section 110 moves along the scalp is inputted to the medical station 200. Such information is used to develop a three dimensional image of the head 2 and the volume that was imaged so that a user is provided with a display of the head and any trauma.

Such an imaging section 110 also includes a light source 112, an array of detection elements 114 and a light skirt 120 (FIG. 3) that extends about the periphery of the imaging section 110. The light skirt 120 is provided and arranged so as to shield the array of detection elements 114 from light that is external to the imaging section 110.

Figure 6:
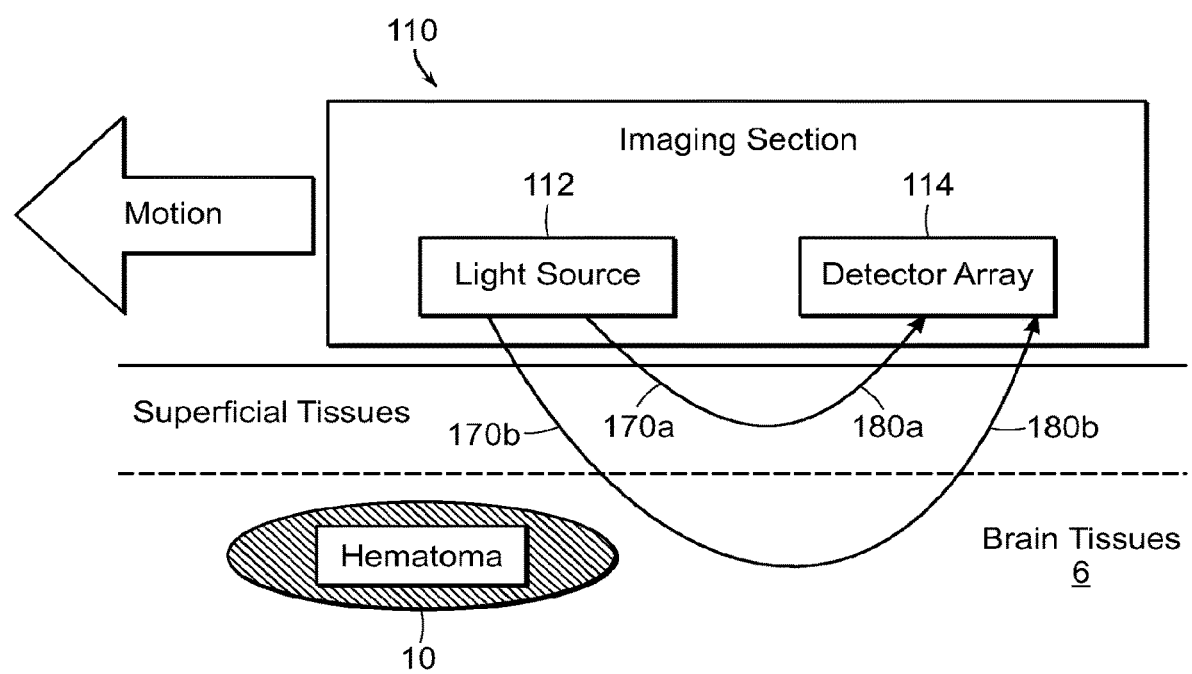
FIG. 6 is another illustrative view of imaging a portion of the head using the handheld detector according to the present disclosure.

In more particular embodiments and as more clearly shown in FIGS. 3 and 6, the light source 114, is configured and arranged so as to include two discrete light sources 112a,b that each emit near infrared light 170a,b and two bands of detection elements 114a,b that are separated from the light sources 112a,b at two different distances to detect reflected light 180a,b. In more particular embodiments, each of the light sources 112a,b is a light emitting diode (LED) emitting light at about a specified wavelength of near infrared light. The light is emitted at two distances from the brain such that the emitted light penetrates to two different depths.

In yet more particular embodiments, the two light sources 112a,b are selected such that they respectively emit near infrared light at about two different wavelengths, a first wavelength and a second wavelength. In more illustrative embodiments, the first wavelength and the second wavelength are on either side of 800 nm and in more particular illustrative embodiments, the first wavelength is in a range that is longer than 800 nm and the second wavelength is the range that is shorter than 800 nm. In exemplary embodiments, the first wavelength is at about 850 nm and the second wavelength is at about 850 nm. As indicated above, the two bands of detector elements 114a,b are arranged so that each band of detector elements 114a,b are positioned so as to detect reflected light 180a,b coming from the two different depths inside the head 2, corresponding to two sensitivity bands 190a,b inside the head. In further embodiments, one of the emitted light 170a penetrates the skull 4 and the other of the emitted light 170b penetrates further inside the skull so as to in effect interrogate the subarachnoid region.

In the present disclosure, the reflected light 180a,b from the two different penetration depths is separately detected by the imaging section 110 and the data corresponding to these two different depths or distances is inputted to the control and monitoring section 150 for processing. The processing circuitry 152 is configured so as to use a ratiometric measure or analysis to detect major blood events (e.g., hematomas) inside the head 2. Such a ratiometric analysis or analysis is used to distinguish the border between normal tissue and tissue in which blood is accumulating, in other words hematoma containing tissue. The ratiometric analysis is a ratio of the densities representing the two depths of penetration.

Such an analysis is performed using any of a number of mathematical techniques known in the art. In one illustrative embodiment, the optical density data from the detector element bands 114a,b is analyzed using a level set method, which is sequentially alternated with a standard matrix inversion. In another illustrative embodiment, a multi-grid approach is used to analyze such optical density data. The multi-grid approach can be advantageous as it should improve the speed of analysis. In further embodiments, noise filtering is applied in either the forward or reverse domain and is selected based upon the expected or discovered noise characteristics.

In use after the detector 100 or imaging section 110 thereof is positioned on the scalp/skull 4 of the patient, the control and monitoring section 150 controls operation of the imaging section so as to cause the light sources 112a,b to continuously emit the near infrared light 170a,b and so that the reflected light 180a,b is continuously monitored by the detector element bands 114a,b.

Also, according to methodology of the present disclosure, the detector 100 or imaging section 110 thereof is moved (see FIG. 6) in a direction transverse to the scalp/skull 4 from a start position to a final or end position. As the detector or imaging section is being so moved, the control and monitoring section 150 causes the imaging section to continuously emit the near infrared light 170a,b, to continuously monitor the reflected light 180a,b using the detector element bands 114a,b and to continuously perform a ratiometric analysis of the acquired optical data at the two different distances.

In further embodiments, the control and monitoring section 150 further evaluates the determined ratio against threshold criterion so as to determine if the tissue is hematoma containing, not hematoma containing or suspect as being possibly hematoma containing tissue. The threshold values are determined using any of a number of techniques known to those skilled in the art. In illustrative embodiments, the threshold values are based on clinical data. In yet further embodiments, a plurality of threshold values are established each being representative of a different patient type, nationality, race and or hair color. In use, the user would initially configure the detector so that the appropriate threshold criterion are used by the control and monitoring section 150.

In yet further embodiments, the control and monitoring section 150 is configured to control operation of the imaging section 110 so that data corresponding to the reflected light 180a,b in the two sensitivity bands 190a,b is outputted in a time sequence to the control and monitoring section. Such data in a time sequence is analyzed by the control and monitoring section 150 to determine if the tissue is hematoma containing, not hematoma containing or suspect as being possibly hematoma containing tissue.

In yet further embodiments, the control and monitoring section 150 includes a plurality of lights or visual indicators 158a-c, that are responsive to control signals from the processing circuitry 152. When the control and monitoring section 150 determines from the optical data that the threshold criterion indicating the presence of hematoma containing tissue is satisfied, the processing circuitry causes one of the visual indicators 158a to be actuated thereby providing a visual queue to the user of the presence of a hematoma. In an illustrative embodiment, the visual indicator 158a outputs red light as a warning or indictor of a hematoma.

In the case where it is determined that the tissue does not contain a hematoma, then the processing circuitry causes another one of the visual indicators 158b to be actuated thereby providing a visual queue to the user that the tissue is normal or not containing a hematoma. In an illustrative embodiment, the visual indicator 158b outputs green light as in indicator of this tissue condition.

There may be cases where the optical data cannot provide a clear determination that the tissue is or is not hematoma containing tissue. In such cases, the processing circuitry causes yet another one of the visual indicators 158c to be actuated thereby providing a visual queue to the user that the tissue is suspect or possibly being hematoma containing tissue. In an illustrative embodiment, the visual indicator 158c outputs another colored light signal (e.g., amber colored) light as in indicator of this tissue condition.

In use, the user can use these three different visual indicators 158a-c as a mechanism to determine what further action should be taken. For example, in the case where it is determined that the tissue being imaged is suspect as possibly being hematoma containing tissue, the user could order further scanning using an appropriate scanner (e.g., MRI or CT scanner) which should be capable of resolving the hematoma containing tissue concern.

Referring now back to FIG. 3, the medical station 200 includes processing circuitry 210 that controls operation and functioning of the medical station and the imaging section as well as allowing the user to manipulate and control processing of the optical data and the results of such processing. As is known to those skilled in the art such processing circuitry 21 includes a processor or other circuit element (e.g., ASIC), RAM, and one or more software programs that is/are executed in the processor so as to perform the control and processing functions of the medical station. The medical station also can embody any of a number of ancillary devices or functionalities, such as for example, a keyboard, mouse, pointer, voice recognition input device and the like that provide mechanisms that allow the user to input commands and additional information as well as to manipulate and visualize data In further embodiments, the medical station 200 includes any of a number of displays 212 that are known to those skilled in the art or hereinafter developed, whereby a visual picture or image can be projected by the display and observed by the user. In exemplary embodiments, such displays include; liquid crystal displays, CRT and plasma screens. In particular embodiments, the created volumetric image is shown using the display 212. Also, the user can use the appropriate ancillary devices to manipulate the volumetric image so as to rotate and/or translate the image so the user can observe the image from different angles or points of view.

In further embodiments, the medical station 200 includes one or more communication mechanisms 204, 206 that are operable coupled to the processing circuitry 210 so that the processing circuitry can receive and/or transmit data or information. In illustrative embodiments, the medical station 200 includes an I/O port(s) 204 as is known to those skilled in the art whereby the detector 100, more specifically an I/O port 154 thereof, can be operably and communicatively coupled to the medical station. In exemplary embodiments, the I/O port 204 is a USB or firewire type of I/O port so that the detector 100 can be connected to the medical station via a hard line 220.

In a further illustrative embodiment, the medical station includes a wireless transmission device 206, such as for example and transceiver and an antenna, that communicates with the detector without the need for a hardline. Such a transmission device 206 is operably coupled to a complimentary transmission device 156 provided with the detector 100. In further embodiments, such transmission devices 206, 156 utilize RF or IR signal techniques for communication. In more particular embodiments, the transmission devices embody well known bluetooth transmission techniques for such wireless communications.

In yet further embodiments, the medical station 200 and/or the detector 100 are configured so as to include an I/O port or wireless communication device that allows either or both of the medical station or the detector 100 to be operably and communicatively coupled to a network (e.g., WAN, LAN). In one illustrative example, the detector 100 and the medical station are each operably coupled to the wired or wireless network using the appropriate techniques and after being so coupled the detector downloads information and/or data to the medical station via the network connections. In another illustrative example, the medical station 200 is operably coupled to the network such that data, information or volumetric image data can be uploaded to medical records.

It is well within the skill of those knowledgeable in the computer or software arts that the structure of the logic of the different methodologies/inventions described herein can be embodied in computer program software for execution on a computer, digital processor or microprocessor. Those skilled in the art will appreciate the structures of the computer program code elements, including logic circuits on an integrated circuit, that function according to the present disclosure, can be developed from the described structure of the logic of the different methodologies/inventions described herein. As such, the present disclosure is practiced in its essential embodiments by a machine component that renders the program code elements in a form that instructs a digital processing apparatus (e.g., computer) to perform a sequence of function step(s) corresponding to the functions and operations of the detector 100 and medical station 200 of the present disclosure as described herein.

Although a preferred embodiment of the disclosure has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A system for detecting a hematoma in tissue of a patient, the apparatus comprising:
   a detection device that emits near infrared light into the tissue and which provides outputs that correspond to detected reflected light the detection device including:
      a near infrared light emitting section that is configured and arranged so the emitted near infrared light penetrates to two different depths wherein a first depth is above the subarachnoid region of the patient and a second depth is below the subarachnoid region of the patient, the near infrared light emitting section includes separate first and second light sources wherein the first light source emits infrared light that penetrates the first depth above the subarachnoid region and the second light source emits infrared light that penetrates the second depth below the subarachnoid region of the patient wherein the first light has a wavelength longer than 800 nm and the second light has a wavelength shorter than 800 nm, and
      a detection section that is configured and arranged so as to separately detect reflected light from the two different depths; and
   wherein the system is configured to apply a ratiometric analysis to the reflected light that is detected while the detection device is moved along an external surface of the tissue to distinguish between normal tissue and tissue containing accumulated blood.

2. The system of claim 1, wherein:
   the detection section is configured and arranged to separately detect reflected light at or about the first wavelength and reflected light at or about the second wavelength.

3. The system of claim 1, wherein:
   the detection device further includes a plurality of tracking devices that each continuously provide time sequenced tracking data of the detection device as it is moved along an external surface of the tissue; and wherein the system is further configured and arranged so as to determine time sequenced positions of the detection device from the time sequenced tracking data from the tracking devices.

4. The system of claim 3, further comprising:
   an imaging section operably coupled to the analysis section;
   wherein the system provides outputs corresponding to the determined time sequenced positions of the detection device; and
   wherein the imaging section is configured and arranged to provide a volumetric image using the acquired time sequence of measured reflected light corresponding to the two different depths and the determined time sequence positions.

5. The system of claim 1, wherein the detection system includes separate first and second detection elements wherein the first detection element detects light reflected from the first depth above the subarachnoid region and the second detection element detects light reflected from the second depth below the subarachnoid region of the patient.

6. The system of claim 5, wherein the first detection element includes a plurality of detection element bands.

7. The system of claim 6, wherein the second detection element includes a plurality of detection element bands.

8. The system as recited in claim 1, wherein the detection device consists of a first imaging section including the infrared light emitting section and the detection section and a separate second control monitoring section for applying the radiometric analysis to the reflected light received by the separate first imaging section.

9. The system as recited in claim 8, wherein the first imaging section is wirelessly coupled to the separate second control monitoring section.

10. A system for detecting a hematoma in tissue of a patient, the apparatus comprising:
    a detection device that emits near infrared light into the tissue and which provides outputs that correspond to detected reflected light the detection device including:
       a near infrared light emitting section that is configured and arranged to simultaneously emit first and second infrared lights wherein the first infrared light penetrates a first depth above the subarachnoid region of the patient and the second infrared light penetrates a second depth below the subarachnoid region of the patient wherein the first light has a wavelength longer than 800 nm and the second light has a wavelength shorter than 800 nm; and
       a detection section that is configured and arranged so as to separately detect reflected light from the two different depths wherein the system is configured to apply a ratiometric analysis to the reflected light that is detected while the detection device is moved along an external surface of the tissue to distinguish between normal tissue and tissue containing accumulated blood.

11. The system of claim 10, wherein the near infrared light emitting section includes separate first and second light sources wherein the first light source emits the first infrared light that penetrates the first depth above the subarachnoid region and the second light source emits the second infrared light that penetrates the second depth below the subarachnoid region of the patient.

12. The system of claim 11, wherein the detection system includes separate first and second detection elements wherein the first detection element detects light reflected from the first depth above the subarachnoid region and the second detection element detects light reflected from the second depth below the subarachnoid region of the patient.

13. The system of claim 11, wherein the first detection element includes a plurality of detection element bands.

14. The system of claim 13, wherein the second detection element includes a plurality of detection element bands.

15. The system as recited in claim 10, wherein the detection device consists of a first imaging section including the infrared light emitting section and the detection system and a separate second control monitoring section for applying the radiometric analysis to the reflected light received by the separate first imaging section.

16. The system as recited in claim 15, wherein the first imaging section is wirelessly coupled to the separate second control monitoring section.

\* \* \* \* \*